(12) United States Patent
Mainz

(10) Patent No.: US 11,673,732 B2
(45) Date of Patent: Jun. 13, 2023

(54) METHOD FOR TREATING THE OPEN CUT EDGES OF PACKAGING MATERIAL FOR THE PRODUCTION OF CARDBOARD/PLASTICS COMPOSITE PACKAGING AND A PACKAGING MATERIAL, A COMPOSITE PACKAGING PRODUCED THEREFROM AND A CONTAINER FOR RECEIVING PACKAGING MATERIAL

(71) Applicant: SIG Technology AG, Neuhausen am Rheinfall (CH)

(72) Inventor: Hans-Willi Mainz, Heinsberg (DE)

(73) Assignee: SIG Technology AG, Neuhausen am Rheinfall (CH)

( * ) Notice: Subject to any disclaimer, the term of this patent is extended or adjusted under 35 U.S.C. 154(b) by 0 days.

(21) Appl. No.: 17/711,312

(22) Filed: Apr. 1, 2022

(65) Prior Publication Data
US 2022/0227562 A1 Jul. 21, 2022

Related U.S. Application Data

(60) Continuation of application No. 16/861,674, filed on Apr. 29, 2020, now Pat. No. 11,358,777, which is a
(Continued)

(30) Foreign Application Priority Data

Jan. 9, 2014 (DE) ..................... 10 2014 100 203.2

(51) Int. Cl.
B65D 81/24 (2006.01)
A61L 2/18 (2006.01)
(Continued)

(52) U.S. Cl.
CPC .............. *B65D 81/24* (2013.01); *A61L 2/186* (2013.01); *B65B 31/042* (2013.01); *B65B 31/08* (2013.01);
(Continued)

(58) Field of Classification Search
CPC ...... B65D 81/24; B65D 85/62; B65D 75/002; B65D 65/42; A61L 2/186; A61L 2/22;
(Continued)

(56) References Cited

U.S. PATENT DOCUMENTS 3,715,860 A 2/1973 Esty
4,061,785 A 12/1977 Nishino et al.
(Continued)

FOREIGN PATENT DOCUMENTS

DE 3235476 A1 5/1983
DE 19748022 A1 5/1998
(Continued)

*Primary Examiner* — Sean E Conley
(74) *Attorney, Agent, or Firm* — The Webb Law Firm

(57) ABSTRACT

A method for treating open cut edges of a packaging sleeve, blank or web material of a packaging material rolled up into a roll, in particular a composite cardboard/plastics material, by applying or introducing a disinfectant-containing treatment agent to or into the outer region of the cut edges. To provide a particularly resource-efficient composite packaging and a production method required for this purpose, it is proposed that at least some of the treatment agent is not applied directly to the cut edges, but that a load carrier is loaded, which load carrier absorbs the treatment agent so that an actively sterilising atmosphere which is created then acts on the open cut edges of the packaging sleeve, blank or web material and performs the desired sterilisation. The invention also relates to a packaging material, to a combi-pack produced therefrom and to a container for receiving the packaging material.

7 Claims, 6 Drawing Sheets

Related U.S. Application Data division of application No. 16/241,623, filed on Jan. 7, 2019, now Pat. No. 10,696,465, which is a division of application No. 15/110,444, filed as application No. PCT/EP2015/050028 on Jan. 5, 2015, now Pat. No. 10,207,852.

(51) Int. Cl.

| | | |
|---|---|---|
| *B65B 31/04* | (2006.01) | |
| *B65B 31/08* | (2006.01) | |
| *B65B 55/10* | (2006.01) | |
| *D21H 27/10* | (2006.01) | |
| *B65D 65/42* | (2006.01) | |
| *B65B 55/04* | (2006.01) | |
| *B65D 75/00* | (2006.01) | |
| *B65D 85/62* | (2006.01) | |
| *A61L 2/22* | (2006.01) | |

(52) U.S. Cl.
CPC .............. *B65B 55/04* (2013.01); *B65B 55/10* (2013.01); *B65D 65/42* (2013.01); *B65D 75/002* (2013.01); *B65D 85/62* (2013.01); *D21H 27/10* (2013.01); *A61L 2/22* (2013.01); *A61L 2202/23* (2013.01)

(58) Field of Classification Search
CPC ... A61L 2202/23; B65B 31/042; B65B 31/08; B65B 55/04; B65B 55/10; D21H 27/10
See application file for complete search history.

(56) References Cited

U.S. PATENT DOCUMENTS

| | | |
|---|---|---|
| 4,631,173 A | 12/1986 | Muller et al. |
| 5,900,111 A | 5/1999 | Nystrom et al. |
| 6,089,368 A | 7/2000 | Lindgren et al. |
| 9,034,253 B2 | 5/2015 | Geissler |
| 9,315,284 B2 | 4/2016 | Floerke et al. |
| 2004/0011688 A1 | 4/2004 | Ishikawa |
| 2006/0269438 A1 | 11/2006 | Lagunas-Solar et al. |
| 2012/0005948 A1 | 1/2012 | Lagunas-Solar et al. |
| 2013/0065958 A1 | 3/2013 | Dunn |

FOREIGN PATENT DOCUMENTS

| | | |
|---|---|---|
| DE | 102009029706 A1 | 12/2010 |
| DE | 102011111523 B3 | 1/2013 |
| JP | 6080456 A | 5/1985 |
| JP | 2000326935 A | 11/2000 |

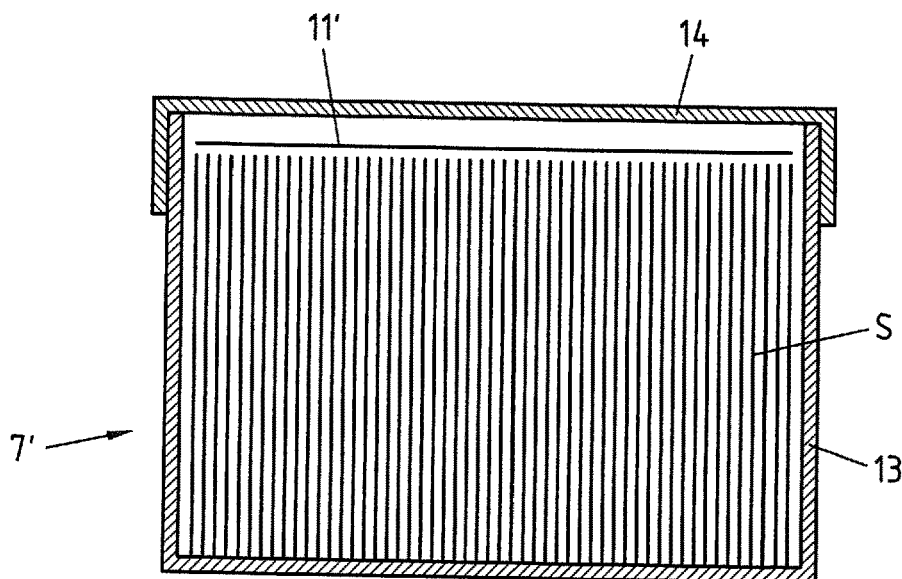
Fig.6
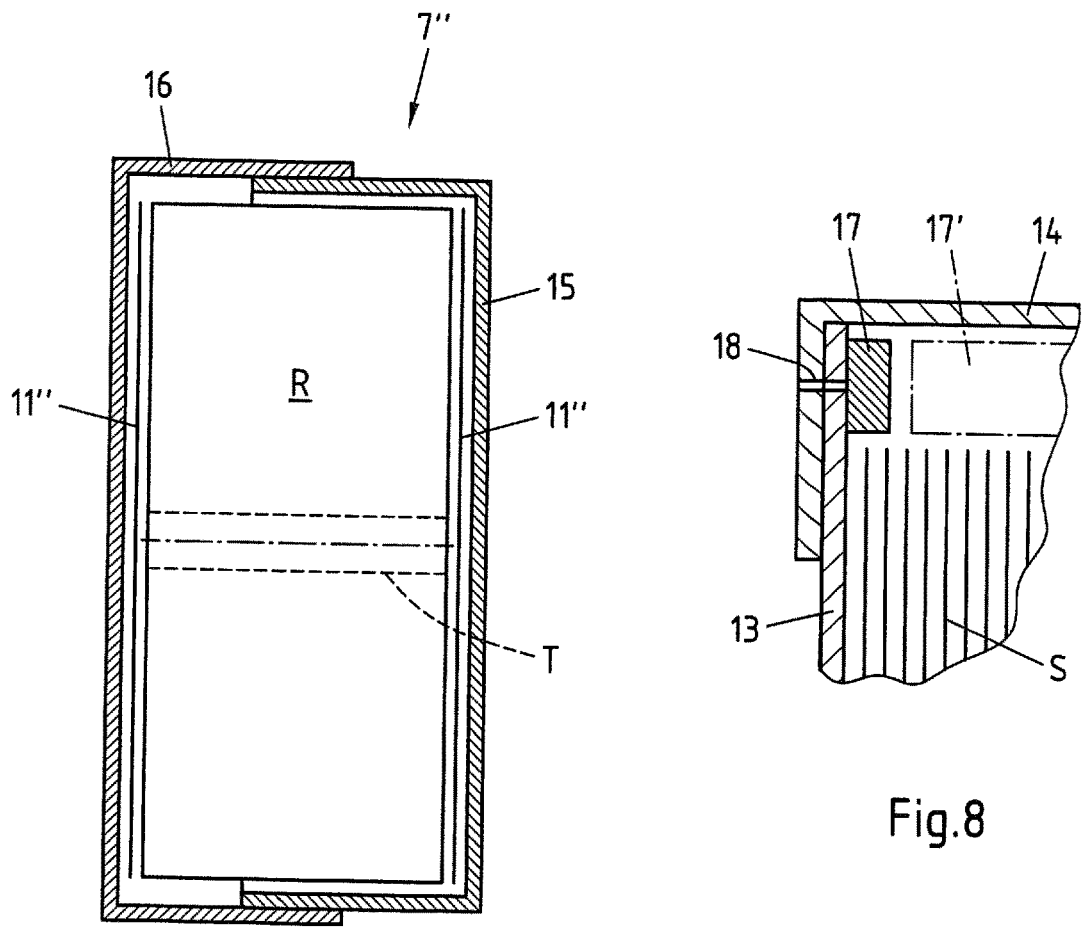
Fig.7
Fig.8

METHOD FOR TREATING THE OPEN CUT EDGES OF PACKAGING MATERIAL FOR THE PRODUCTION OF CARDBOARD/PLASTICS COMPOSITE PACKAGING AND A PACKAGING MATERIAL, A COMPOSITE PACKAGING PRODUCED THEREFROM AND A CONTAINER FOR RECEIVING PACKAGING MATERIAL

CROSS-REFERENCE TO RELATED APPLICATIONS

This application is a continuation of U.S. patent application Ser. No. 16/861,674, filed Apr. 29, 2020, which is a divisional of U.S. patent application Ser. No. 16/241,623 filed Jan. 7, 2019 and now U.S. Pat. No. 10,696,465, which is a divisional of U.S. patent application Ser. No. 15/110,444 filed Jul. 8, 2016 and now U.S. Pat. No. 10,207,852, which is the United States national phase of International Application No. PCT/EP2015/050028 filed Jan. 5, 2015, and claims priority to German Patent Application No. 10 2014 100 203.2 filed Jan. 9, 2014, the disclosures of all of which are hereby incorporated by reference in their entireties.

BACKGROUND OF THE INVENTION

The invention relates first of all to a method for treating open cut edges of a packaging sleeve, a blank or a web material of a packaging material, rolled up into a roll, in particular of a cardboard/plastics composite material, by applying or introducing a disinfectant-containing treatment agent to or into the outer region of the cut edges.

The invention also relates to a correspondingly sterilised packaging material for the production of a packaging, in particular of a beverage carton, substantially consisting of a composite material with a pulp/cardboard layer, to a composite packaging produced therefrom and to suitable containers for receiving packaging material.

When the expression "open cut edges" is used in the following, it means not only the cut edges which delimit a blank or a packaging sleeve formed therefrom, but also all "open" pulp regions which are exposable to the surrounding atmosphere, so that in particular cut edges inside perforations are also meant, as are found in beverage packagings in the region of pouring elements to be applied or other opening aids.

Cardboard/plastics composite packagings are either produced in the so-called "tubular forming process" from a roll or are produced from individual blanks of paper/plastics laminate material. Here, individual blanks are initially obtained from a roll of composite material and are then provided with a tight longitudinal seam which is generally produced by folding and sealing the composite material and, if appropriate, by additionally overbonding with a sealing strip.

The further processing of packaging sleeves produced in this manner, i.e. the unilateral closure at the top or bottom of the subsequent packaging, sterilisation, filling and re-closure is generally performed directly in the filling machine.

The steps of cup formation, cleaning and, if appropriate, disinfection are carried out here before the filling material is poured in and the composite packaging is closed and finally shaped. During production of a so-called aseptic composite packaging, the disinfection and filling procedures are carried out in the aseptic zone of a filling machine. If the cup is formed before the disinfection or sterilisation step, it can also be formed outside the aseptic zone. Methods of this type are described, inter alia, in DE 32 35 476 A1 and in DE 10 2009 029 706 A1.

Irrespective of the production method, the packaging is usually closed by compressing and sealing the edges of the packaging material, for example, by ultrasound using a sonotrode and an anvil. Other methods for closing the packaging are also known, for example electromagnetic induction or charging with hot air in conjunction with mechanical pressing.

It has been found that dust in particular is responsible for bacterial contamination, so that the primary objective of all steps should be to avoid dust. This can be carried out by the suction-removal of dust during production of the packaging sleeve and by reducing the lifetime of the cutting blades which are used. However, due to the fibres in the pulp of the cardboard which is used, the open cut edges always remain the "problem areas" in the production of the packaging. Although in most cases, efficient suction installations are helpful here, the high energy costs and noise emissions thereof put a strain on the production process.

An "aseptic packaging" is understood as meaning a packaging into which a filling material, particularly a foodstuff, is filled under aseptic conditions. Filling machines used for this purpose comprise an aseptic zone, a type of clean room, in which sterile, i.e. germfree conditions prevail and which is generally maintained by the closed or substantially closed configuration thereof, except for a few openings. The clean room atmosphere created therein is also under overpressure due to the introduction of sterile air, thereby preventing the entry of germs from outside. The packaging material is then transported continuously or discontinuously through the aseptic zone, being successively sterilised, dried and filled and closed in one or more steps. Contemporary prior art machines, for example a machine from the 24 series by the Applicant, allow per processing step a processing time of an individual sterilisation or filling station of approximately 0.6 seconds to approximately 0.85 seconds, subject to the packaging format.

The edges of packaging sleeves are open cut edges of an otherwise water-tight laminate material which may also have an oxygen barrier. Therefore, the risk of bacterial exchange (microorganisms and spores) exists primarily in the region of the edges, as a result of which the bacterial load of the material can increase and ultimately contamination of the product cannot be ruled out either during the subsequent filling procedure of the packaging or during the closing procedure for producing the finished packaging.

Closing a unilaterally open, full container consisting of composite material entails the risk that if the material is sealed by ultrasound in particular, dust from the packaging material can be projected out of the open cut edges and can contaminate both the aseptic region of the filling machine and the open packaging itself.

Single-cell organisms which are capable of replication by cell division and which can replicate in the filling material ("product") of a packaging and, in so doing, are capable of altering the characteristics of the filling material are understood as vegetative microorganisms. The term also includes the survival forms of the replication-competent single-cell organisms, such as the spores thereof.

These spores are generally very resistant to changes in the environmental conditions surrounding them. If microorganisms do not find an environment for metabolism and/or multiplication, some microorganisms can be converted into a spore stage.

More precisely, in the context of the present application, the term "microorganisms" is understood as meaning eukaryotes and prokaryotes, eukaryotes having a true cell wall and comprising algae, protozoans, fungi and slime mould, while prokaryotes cover the group of bacteria (cf. "Bergey's Manual of Determinative Bacteriology", 8th Edition, Baltimore: Williams & Wilkins, 1974).

Survival forms such as spores are known specifically in the case of prokaryotes. For example, even after the thermal and/or chemical treatments of raw materials for the production of raw cardboard products, spores can be found to an increasing extent precisely in these products, since treatment methods of this type either kill off the directly replication-competent form of the microorganisms or initiate conversion into the spore form.

The expression "colony-forming unit per gram" (CFU/g) is known to a person skilled in the art as an indication of the number or quantity of microorganisms contained in an amount of substance (for example in the raw cardboard product mentioned). Unlike the direct counting of all present microorganisms using a suitable optical means, the number of colony-forming units is determined by the deliberate reproduction of dividable microorganisms which are present under suitable cultivation conditions. This is generally carried out up to a colony size which can be counted by unmagnified vision. In this respect, use is made of the fact that precisely one colony is produced from each individual dividable microorganism under previously defined conditions. Individual cases in which two CFU are positioned so closely together that only one visible colony is formed therefrom are then routinely disregarded.

Determination methods which are typical in microbiology are regulated by ISO 8784-1 from 2005.

Thus, a reduction in the CFU/g is used by a person skilled in the art as an indication of the efficiency of a method for bacteria reduction and is often called the disinfection rate. Derived therefrom is the sterility rate to be counted via the number of produced packagings.

It is known from DE 10 2011 111 523 A1 to treat cut edges, open at the top or bottom, of a packaging sleeve of a packaging material by applying a treatment agent which contains a disinfectant, the disinfectant remaining on the cut edges after application and penetrating inside the packaging material. The treatment agent is respectively applied by being sprayed from above, a plurality of packaging sleeves being combined in a folded-flat state. In this known method, the treatment agent is applied to the edges of the packaging sleeve in a station, constructed specifically for this purpose, in one or more separate method steps immediately before the packaging sleeves are packed into a covering box. This approach is relatively complex. There is also the risk that the treatment agent will be accidentally sprayed beyond the packaging. Additionally, it has been found that the outsides of the packaging sleeves can quickly be affected. For example, the treatment agent can act in an undesirable manner on the printed image on the outside of the packaging sleeve and can damage it. It can also happen that two packaging sleeves remain stuck to one another after being removed from the covering box and can disrupt production during their further processing in the filling machine.

On this basis, the object of the invention is to provide a particularly resource-efficient composite packaging and a production method required for this purpose.

SUMMARY OF THE INVENTION

With regard to the method, this object is achieved in that at least some of the treatment agent is not applied directly to the cut edges, but a load carrier is loaded, which load carrier absorbs the treatment agent so that an actively sterilising atmosphere which is created then acts on the open cut edges of the packaging sleeve, blank or web material and performs the desired sterilisation.

In this respect, sterilisation can be achieved up to an adequate depth in the cardboard, without the known and approved execution of the packaging production being affected. The "adequate depth" is determined by the respectively used production method. If the seam is formed by ultrasound, sterilisation must be carried out to a depth of approximately 2 to 3 mm to reliably rule out contaminated dust from being propelled out of the open edge during the sealing procedure. If the seam is closed by microwave technology, a depth of a few tenths of a millimetre is also sufficient.

The treatment agent or at least some of the treatment agent is preferably transferred indirectly by evaporation and subsequent absorption in the open cut edge(s).

A further teaching of the invention provides that the actively sterilising atmosphere which is created is separated from the surroundings by a container. In this respect, at least parts of the container, preferably parts of the inside, are preferably wetted with treatment agent.

In a further configuration of the invention, the container is a covering box used for storing and/or transporting the packaging sleeve or packaging sleeves, the blank(s) or the roll(s). In this respect, according to a further configuration of the invention, at least partial regions of an inside of the covering box are wetted with treatment agent.

During the exemplary production of paper/plastics composite packaging material, a carrier layer, generally paper or cardboard, is firstly coated and the composite material is produced in this manner. The composite material is then printed before crease lines and fold lines are introduced. After these processing steps, the web material is generally present as rolled material and can then be treated within the context of the present invention. However, before a treatment according to the method of the invention, first of all in a further step, blanks are preferably punched out of the web material and stacked in layers. From these blanks, it is then possible to produce, by folding and joining the side cut edges (longitudinal seam sealing) packaging sleeves which are open at the top and bottom which can be sent, in a flat-folded and packed state, to the filling plants. The method according to the invention is preferably carried out in connection with the packing of the packaging sleeves and is thus not carried out in the aseptic region of a filling machine, but instead outside the filling machine.

If the packaging sleeves or blanks are to be produced from rolled up web material, the method according to the invention can be applied before individual blanks are cut to length if the planar end faces of the cylindrical roll which respectively consist completely of an open cut edge are sterilised accordingly.

If the packagings are to be directly produced from rolled up web material, the end faces of the cylindrical roll which respectively consist completely of an open cut edge can be sterilised accordingly.

An incubation time for the disinfectant is to be expediently provided. Said incubation time is usually within a range of a few minutes to several hours and is adequate to ensure the disinfection of the edges during the transportation time of the blanks, packaging sleeves and rolled up web material to a filling machine. The treatment agent usually remains permanently in the packaging material. The edge regions of the blanks, packaging sleeves and rolled up web material then remain germ-free for a period of many days to a few months.

With regard to a product, i.e. to a packaging material and to a, particularly aseptic, packaging formed therefrom, the object of the invention is achieved in that the at least one layer of pulp/cardboard has a first partial region and at least one second partial region, the first partial region having a load of at least 100 colony-forming units per gram of pulp/cardboard and the at least one second partial region having a load of at most half the colony-forming units per gram of pulp/cardboard compared to the first partial region.

Reference is made to the more detailed description, provided further below, of the determination method specified here for a more precise definition of the mentioned features.

Due to the configuration of a packaging material having the features according to the invention, it is possible to produce high-quality composite packagings which reliably protect the filling material contained therein for a long period of time, without having to form the composite material on a pulp/cardboard layer which has a load of less than 100 CFU/g. Consequently, it is also possible to significantly improve the environmental balance of a composite packaging model. As a result of the lower demands made on the pulp/cardboard layer in respect of the bacterial load thereof, it is possible to process cardboard qualities which are produced using considerably fewer chemicals.

In a particular configuration of the invention, the first partial region even has a load of at least 250 CFU/g, preferably at least 500 CFU/g, particularly preferably at least 1000 CFU/g.

Consequently, the environment is protected to a particular extent, because the production process of conventional specific types of cardboard for beverage cartons has to rely significantly on the use of polluting chemicals and furthermore the energy requirement is also higher compared to a standard cardboard production.

At least one open cut edge of the respective packaging sleeves is adequately penetrated by disinfectant. This means that the peripheral regions established on the cut edges and forming the at least one second partial region are reduced to an adequately low bacterial load of at most half.

The "peripheral region of a cut edge" is understood as meaning those regions which are in contact with an open edge or are delimited by an open edge, and a peripheral region should be at least 0.3 mm deep, preferably at least 1.5 mm deep. To be able to rule out particularly reliably a contamination of foodstuffs in an aseptic packaging, it is even preferred that the peripheral region is up to 2 mm thick, preferably even up to 3 mm thick or even up to 5 mm thick.

The area ratio between the first and the at least one second partial region or, if there is a plurality of second partial surfaces, between the entire surface of the second partial surfaces is preferably between approximately 8:1 to approximately 60:1. In this respect, the at least one second partial region always forms a defined shape, preferably a ring surface or a strip shape. The size of the surface depends on the format of the (subsequent) composite packaging and on the width of the peripheral region forming the at least one second partial region, i.e. it depends on the penetration depth of the treatment agent (measured from the cut edge into the interior of the surface of the packaging material).

Based on a specific packaging format or on a specific type of packaging, the distribution between the first and the at least one second partial region forms a repetitive pattern. This means that the first and the at least one second partial regions are in particular not distributed randomly over the unrolling of a composite packaging, but instead they follow a type-based repetitive pattern. For example, the surface of an unrolled composite packaging can form a rectangle. The surface can be filled by the first partial region up to an individual second partial region formed by a peripheral region extending along one of the four edges. If there are provided for the corresponding composite packaging type two second partial regions, these can be formed by peripheral regions on opposite edges or on edges which abut one another at a right angle. It is also possible that all four peripheral regions delimited by a respective edge form a second partial region and thereby completely frame the first partial region. If a, for example, circular perforation is provided inside the surface formed by the first partial region, it is possible that an annular second partial region as a peripheral region abuts on or around the edge formed by the perforation. The position of this second partial region is also repeated regularly within the series of a composite packaging type.

A further teaching of the invention provides that the at least one layer of pulp/cardboard has portions of recycled fibres.

For sensitive uses, such as the packaging of foodstuffs, cardboard webs with contents of recycled fibres have hitherto been impossible, because these webs can have indefinable qualities and quantities of impurities or contaminants. Due to the use of the method or product according to the invention, these ecologically meaningful resources which are adequately available virtually worldwide can also be used for the first time to protect foodstuffs which are to be packaged aseptically, thus in particular so-called UHT milk.

Another configuration of the invention provides that, compared to the first partial region, the second partial region has a load of at most a quarter, preferably a tenth, most preferably a hundredth of colony-forming units per gram of pulp/cardboard. It is even possible for the load of colony-forming units per gram of pulp/cardboard to be able to assume even substantially smaller fractions. Consequently, the risk of contamination to the filling material is further reduced.

According to a further configuration of the invention, the peripheral regions located on the cut edges have a maximum of 10 CFU/g, preferably a maximum of 5 CFU/g, and most preferably less than 1 CFU/g. As a result, extremely good sterilisation rates can be achieved. Furthermore, particularly in the case of aluminium-free composites, the storage life of the finished packaging and of the filling material to be protected thereby can also be increased.

According to a further teaching of the invention, at least one of the second partial regions is delimited by an open cut edge or by perforated edges. In this respect, the "peripheral region" which results along the open cut edges or perforated edges and has been penetrated by disinfectant, is at least 0.3 mm thick, in particular 1.5 mm thick and particularly preferably at least 2 mm thick.

The second partial region is preferably delimited from the first partial region by an imaginary line running substantially parallel to the cut or perforated edge delimiting the second partial region.

The treatment agent is preferably transferred indirectly by evaporation and subsequent absorption in the open cut edge(s) of the packaging material. For this purpose, in particular at least partial regions of the inside of a container, in particular of a covering box are wetted with treatment agent or carrier elements to be inserted into or affixed in the container are used as load carriers.

All or selected parts of the inside of the container particularly of an outer packaging (covering box or load carriers inserted or affixed therein) can be loaded with treatment agent, thus in particular with a sterilisation solution before or after the container is closed. This is preferably carried out before closure.

If the container is a covering box of corrugated board, this provides the advantage that the sterilising agent is absorbed from the loaded covering box flaps through the upper or lower open cardboard edges of the packaged sleeves in the covering box. The work load which is already significantly reduced compared to a sterilisation of packaging sleeves according to DE 10 2011 111 523 A1 can be further reduced if the covering box is subjected to the treatment agent outside the direct production line, for example in an adjacent room. In this respect, it can occasionally even be particularly preferred if the covering box, present as a folding box, is loaded before or while it is folded up.

An "injecting" of the atmosphere enclosed by the container, preferably by the covering box after the carton has been closed is possible, for example using a needle, and the covering box has to be pierced once or several times in appropriate areas, for example in the free headspace. It is also possible for a load carrier, for example a felt strip, to be applied to the inside of the covering box before it is closed and, after it has been closed, it is possible for it to be pierced by a needle so that the needle can inject the treatment agent into the load carrier. In this manner, the surroundings are practically not polluted by the active ingredients contained in the treatment agent.

For this purpose, in a further configuration of the invention, the container can also comprise a valve. The use of a valve effectively prevents the treatment agent from re-issuing from the container and prevents an excessive diffusion. The valve can be configured as a mechanical one-way valve or as a pierceable and self-closing membrane. The provision of a mechanical valve can be particularly advantageous in the case of reusable containers, while a self-closing membrane can also be affixed very easily to the container from the outside or inside and affords adequate protection at least for a single use.

The treatment agent is preferably coloured with an appropriate dye. Consequently, it is easy to establish visually where it has been applied. This can be used for control purposes. Furthermore, if a dye is used which is absorbed together with the disinfectant by the open cut edges of the packaging material from the actively sterilising atmosphere, it is also possible to verify from the packaging material itself by means of a simple visual check that the treatment has been completed. In this respect, the penetration depth of the treatment agent into the peripheral region can also be seen. It is thus preferred that the dye produces a discoloration of the treated edges.

A further teaching of the invention provides that the composite packaging according to the invention is produced from the packaging material.

A container according to the invention for receiving a plurality of flat-folded packaging sleeves, blanks or web material rolled up into a roll is characterised in that at least parts of the inside of the container are wetted or provided with treatment agent and/or load carriers provided with a treatment agent are provided inside the container. Furthermore, the preferably outer surfaces of the container can be sealed at least in the perforated region to reliably prevent a migration of the treatment agent into the surroundings. Containers according to the invention are described in more detail further below with reference to the embodiments.

An outer packaging can be loaded in a suitable area, for example on the insides of the flaps of a covering box, with a treatment agent containing a disinfectant, for example a peroxide solution by spraying, dripping and subsequent spreading, coating, rolling, dabbing, spatulating, printing (for example by an "inkjet" method), dipping or evaporating. The loading procedure can also be carried out as an injection, as already mentioned.

The edges of the packaging materials, to be transported in a container, can also be loaded with disinfectant by applying a strip, an insert sheet or other carrier materials loaded with sterilising agent.

In this respect, it can be advantageous if the load carrier is configured as an accumulator and can be refilled with liquid treatment agent in order to then re-release the treatment agent into the surroundings. In particular, porous or cellular storage materials are suitable for this purpose.

The flat-folded packaging materials, packed in a container, particularly in a covering box are generally transported for a period of several days. Meanwhile, a bacterial reduction or sterilisation of the open cardboard edges and of the container or the outer packaging takes place by the absorbed sterilisation agent. In this respect, it has surprisingly been found that in spite of very low concentrations of disinfectant, outstanding disinfection rates are achieved. It is assumed that the low concentrations of disinfectant can use the long residence time in the container as effective exposure time. The actively sterilising atmosphere which is created can thus be maintained within an effective scope for a long period of time of several hours or even days. Thus, a long exposure time at a low concentration is obtained. The disinfectant penetrates the peripheral region or perforated region of the cardboard by up to 2 mm or 3 mm or even deeper, subject to the quantity used. This is important, because the fibres located there in the pulp/cardboard layer are denoted as non-stationary and thereby the germs on the fibres are also not bound, but can escape as dust with the fibres from the pulp/cardboard layer.

The exposure time is subject to the treatment agent used and to the additions contained therein, to the dosage, the expected disinfection rate and to the ambient temperature, in each case based on a specific type and grammage of cardboard.

An absorption of treatment agent through the edge of the cardboard is possible, since the cardboard used for the packagings to be produced is hydrophilic, and as a finished product generally has a relative moisture content of approximately 5.5. % to 8.5%, i.e. the moisture content of the cardboard is well below the saturation limit resulting from the prevailing environmental conditions and is generally identical to the equilibrium moisture relative to the surroundings.

The addition of a polar organic solvent which has a lower vapour pressure than the active agent, thus here the disinfectant, acts as an accelerator. Thus, the addition of ethanol to, for example, a peroxide solution promotes the absorption action of the cut edge and increases the penetration of the peroxide into the cardboard. This allows a deeper penetration of the disinfectant into the cut edges, so that with a suitable ratio of disinfectant to ethanol, a peripheral region of the packaging material to be treated can be sterilised as far as a depth of several millimetres even after a few hours.

Ethanol belongs to the group of polar organic solvents which generally act as accelerators if the vapour pressure thereof is lower than that of the active medium. If the vapour pressure of the admixed polar organic solvent is higher than that of the active medium, the solvent acts as a retarder. An example of a solvent having a higher vapour pressure is DOWANOL®, a branded product belonging to DOW Chemical Company. In general, it can be stated that low-molecular polar organic solvents have a low vapour pressure and higher-molecular organic solvents have a high vapour pressure.

In addition, the sterilisation effect of some sterilising agents is intensified synergistically.

Determination Method:

The following determination method is set out to provide a more precise definition of the features mentioned in the claims:

Determination of the Colony-Forming Units Per Gram (CFU/g)

The European standard method ISO 8784-1:2005 and the references stated in these test regulations are chosen as a basis for determining the colony-forming units per gram (CFU/g). The test regulations are applied here for investigating the CFU/g load of packaging material or composite material consisting of cardboard, plastics and occasionally aluminium. If deviations from the cited test regulations are necessary when carrying out the sampling and determination of the CFU/g of the packaging material, they will be explained in the following.

1.1.1 Sampling and Sample Preparation

The samples of packaging material which are taken must not be touched by hand. They are stored in sterile sampling vessels, preferably in sterile plastics bags. The regions to be examined are cut into pieces using sterile scissors. "Regions to be examined" are:
  a. The first partial region, which is not a peripheral region (sample removed at least 10 millimetres from the open cut edge)
  b. The second partial region or peripheral region, on the open cut edges or the perforated edges of the packaging material
  (up to at most three millimetres from the open cut edge)

To supplement the European standard method ISO 8784-1:2005, chapter 8 "Preparation of the test material", a maximum of 3 g packaging material are used for the first partial regions. A maximum of 3 g packaging material are also used for the second partial region. If insufficient material is obtained from a sample, the second partial regions of a maximum of 5 identical samples are used together.

1.2 Optional Determination of the Surface Bacterial Count

It is possible that, before sampling, the specimens of packaging material are also contaminated on the surface in addition to the internal presence of germs. It is possible to prevent an error in determining the CFU/g of the packaging material by determining the surface bacterial count separately and subtracting the surface bacterial count from the numerical value, determined under 1.1, of the colony-forming units per gram.

1.2.1 Terms and Abbreviations
ml=millilitre
h=hour
CFU=colony-forming units
° C.=degrees Celsius
g=gram
mm=millimetre
cm=centimetre 1.2.2 Required Aids and Appliances
Contact petri dishes (plastics) ∅ 5.5 cm (for example Greiner Bio-One 629180)
Tweezers
Cutter blade
Sterile plastics bag or aluminium foil
Steriliser
Incubator
Sterile workbench
Culture media: plate count agar (for example available as Oxoid No. CM 325, Merck No. 105463, Difco No. 247940)

1.2.3 Implementation

240 $cm^2$ of packaging material area are tested per sample. A contact petri dish has an area of 24 $cm^2$. Therefore, 10 contact dishes per sample are to be prepared in order to examine the above-mentioned area.

Introduced into the sterile petri dishes is enough culture medium for the agar to project over the edge of the petri dish (arching), but not to run out beyond the edge. The prepared cooled contact dishes are pressed onto the surface of the packaging material, closed and incubated under the specified conditions.

Care should be taken that the samples are touched only by sterile tweezers and the contact dishes do not come into contact with the open edge of the packaging.

The petri dishes are placed into the incubator with the lid downwards to prevent the formation of condensation.

Culture medium: plate count agar is used for the surface bacterial count.

Incubation: the plate count agar is incubated for 5 days at 30° C., the evaluation being carried out subsequently thereto.

1.2.4 Evaluation

All the colonies present on the contact plates of a sample are counted. The results are converted to CFU (colony-forming units)/100 $cm^2$ and recorded. The value obtained is converted into the surface of the regions to be investigated and is subtracted as a numerical value from the value of the colony-forming units per gram.

EXAMPLES

For the practical implementation of the method according to the invention, for example a hydrogen peroxide solution of 3.5% to 50% can be used as the treatment agent with or without the addition of:
  Evaporation retarder (for example DOWANOL®)
  surface tension-reducing agents, for example alcohol portions (alcohol portions with retarder, surface-active substances such as surfactants, etc.)
  peracetic acid 3-15%
  n- or isopropanol
  other sporicidally active agents.

The solution can be processed in admixture with water or alcohol (ethanol), in this respect it is without toxic residues or is completely volatilisable. Of course, the treatment agent can also have another suitable disinfectant as a substitute for the hydrogen peroxide solution.

12 examples of use are stated in Table 1. The following basic conditions apply to these examples:

The CFU/g was evaluated according to the standards and processes described in the methods. The treated packaging material has as the cardboard layer a cardboard by Stora Enso Natura Board with a grammage of 230 g/m2. Unless indicated otherwise, 350 packaging sleeves were stored in one container.

The Containers have the Following Characteristics:
Covering box: container produced from corrugated board, with dimensions of W: 60 cm; H: 19 cm; D: 10.5 cm
Plastics box: lidded container produced from polypropylene, with dimensions of W: 60 cm; H: 19 cm; D: 10.5 cm
Shrink film: film produced from polyolefins, with dimensions of W: 1 m; L: 2.5 m; thickness: 20 μm
Loaded paper carrier: DIN A4, pulp with a grammage of 150 $g/m^2$ The treatment agent is produced from the following chemicals:

$H_2O_2$ solution: Peroxal DS 35% $H_2O_2$ solution (foodstuff quality)
Ethanol: industrial ethanol (99%) methylated with MEK (1%)
Methanol: industrial methanol (98%)
Dowanol: 1-methoxy-propanol-2 by Dow Due to minimal absorption amounts, there are no detectable residual quantities of disinfectant, for example residual quantities of peroxide, before the packaging material is processed in the filling machine. Therefore, a risk to health is ruled out.

TABLE 1

Investigation of different examples of use:

| | Treatment agent | Volume proportion | Applied volume | Type of application | Container | Untreated* | 1 h exposure time* | 48 h exposure time* |
|---|---|---|---|---|---|---|---|---|
| Example 1 | $H_2O_2$-solution<br>Ethanol<br>Water | 1<br>1<br>1 | 1 ml | Spreading over flap of covering box | Covering box | -- | - | ++ |
| Example 2 | $H_2O_2$-solution<br>Ethanol<br>Water | 10<br>1<br>1 | 10 ml | Spreading over flap of covering box | Covering box | -- | + | +++ |
| Example 3 | $H_2O_2$-solution<br>Ethanol<br>Water | 1<br>5<br>5 | 5 ml | Spreading over flap of covering box | Covering box | -- | - | + |
| Example 4 | $H_2O_2$-solution<br>Ethanol<br>Water | 2<br>2<br>1 | 2 ml | Spreading over flap of covering box | Covering box | --- | - | +++ |
| Example 5 | $H_2O_2$-solution<br>Ethanol<br>Water | 2<br>2<br>1 | 5 ml | Spreading over flap of covering box | Covering box | --- | + | +++ |
| Example 6 | $H_2O_2$-solution<br>Ethanol<br>Water | 1<br>1<br>1 | 1 ml | Spreading over flap of covering box | Covering box | -- | - | ++ |
| Example 7 | $H_2O_2$-solution<br>Ethanol<br>Water | 2<br>2<br>1 | 1 ml | Loaded paper carrier | Plastics box | -- | - | +++ |
| Example 8 | $H_2O_2$-solution<br>Ethanol<br>Water | 2<br>2<br>1 | 2 ml | Loaded paper carrier | Covering box | -- | - | ++ |
| Example 9 | $H_2O_2$-solution<br>Ethanol<br>Water | 2<br>2<br>1 | 2 ml | Loaded paper carrier | Shrink film | -- | - | +++ |
| Example 10 | $H_2O_2$-solution<br>Ethanol<br>Water | 1<br>1<br>5 | 1 ml | Spreading over flap of covering box | Covering box | -- | -- | - |
| Example 11 | $H_2O_2$-solution<br>Ethanol<br>Water | 1<br>1<br>1 | 1 ml | Spreading over flap of covering box | Covering box | -- | - | ++ |
| Example 12 | $H_2O_2$-solution<br>Dowanol<br>Water | 1<br>1<br>1 | 1 ml | Spreading over flap of covering box | Covering box | -- | -- | - |

*CFUs in the defined peripheral region (up to 3 mm) of the open cut edge of the packaging material

| Legend: | --- | >1000 CFU/g | + | <50 CFU/g |
|---|---|---|---|---|
| | -- | 500 CFU/g < x < 1000 CFU/g | ++ | <10 CFU/g |
| | - | 100 CFU/g < x < 500 CFU/g | +++ | <1 CFU/g |

To summarise, the advantages of the invention can be outlined as follows:

Treatment agent can be applied in a defined manner to the covering box flaps.

Minimum consumption of disinfectant compared to directly spraying the edges. Potential risk to and contamination of the working environment is significantly reduced thereby.

Overloading by direct spraying is avoided.

Time for absorption exchange between cardboard flap/sleeve edge or perforation is adequately provided by transportation from production site to filling station (frequently more than 3 days).

Identification by dyeing the treatment agent on the covering box flaps, therefore a good application and dosing control is possible.

No influence on the visible region of the outside of the packaging. In particular, the printed image which is important for the sale of the composite packaging is not affected and adjacent packaging sleeves are effectively prevented from sticking together when fed to a filling machine.

The treatment agent, particularly the peroxide solution, acts practically exclusively on the open cut edges because it is actively absorbed thereby. No load on the rest of the packaging.

In the following, the invention will be described in more detail with reference to drawings which just illustrate embodiments.

BRIEF DESCRIPTION OF THE DRAWINGS

FIG. 6 is a vertical sectional view of another embodiment of a container,
FIG. 7 is a vertical sectional view of a container for receiving a roll of packaging material,
and FIG. 8 is a detail view of a corner of a container with a carrier element fastened inside.

DETAILED DESCRIPTION OF THE INVENTION

Figure 1A:
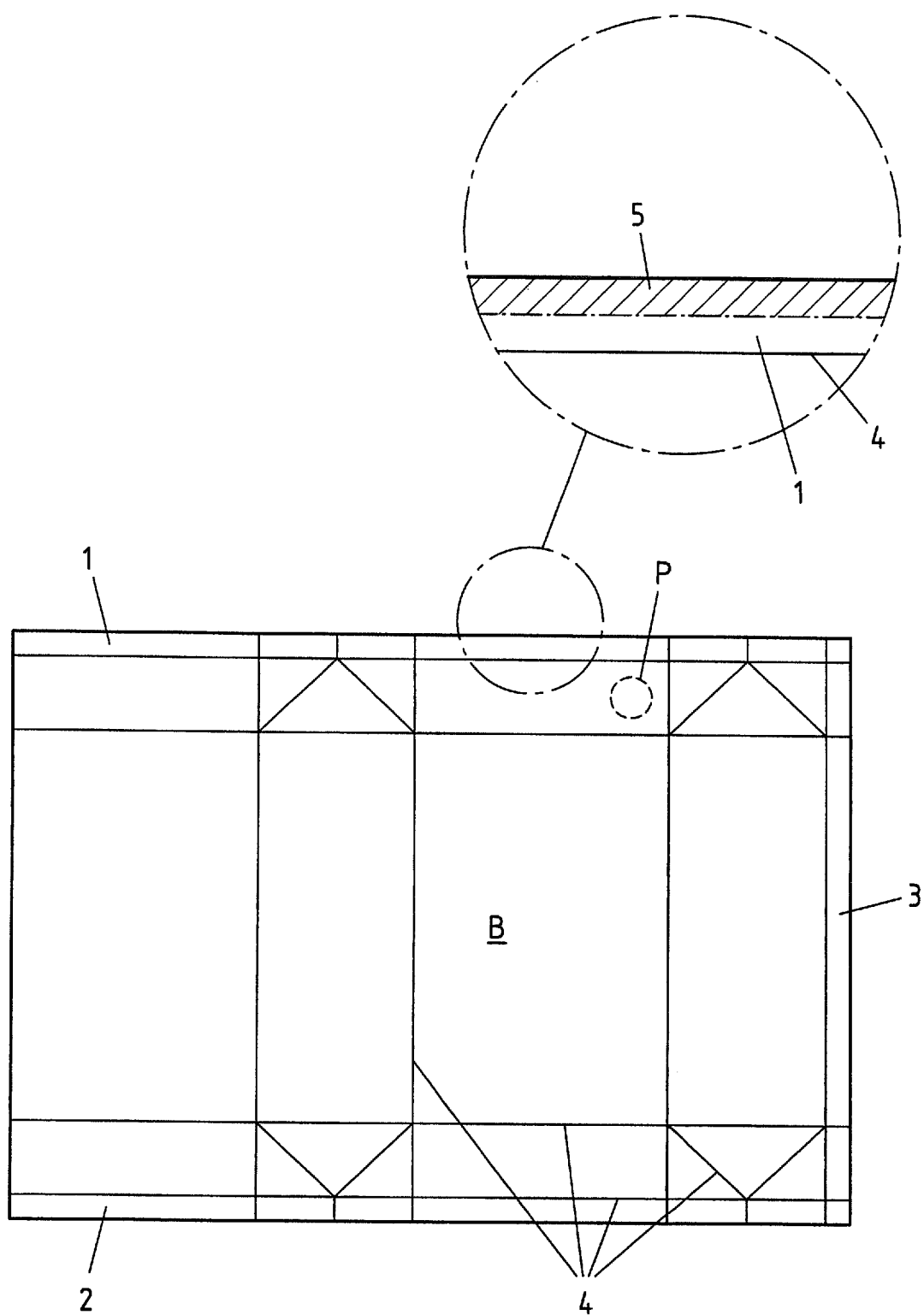
FIG. 1A is a plan view of a blank for beverage cartons.

FIG. 1A shows a blank B which is produced from a composite laminate and has three zones 1, 2, 3 at the top, bottom and on its right side for the later seam production and is also provided with a plurality of crease and fold lines 4 which facilitate the later folding up of the finished beverage carton and of which only a few have been provided with reference numeral 4 in FIG. 1A. On the top of the blank B, a round perforation P has been provided as a weakened zone for a pouring element (not shown) which is to be applied.

Figure 1B:
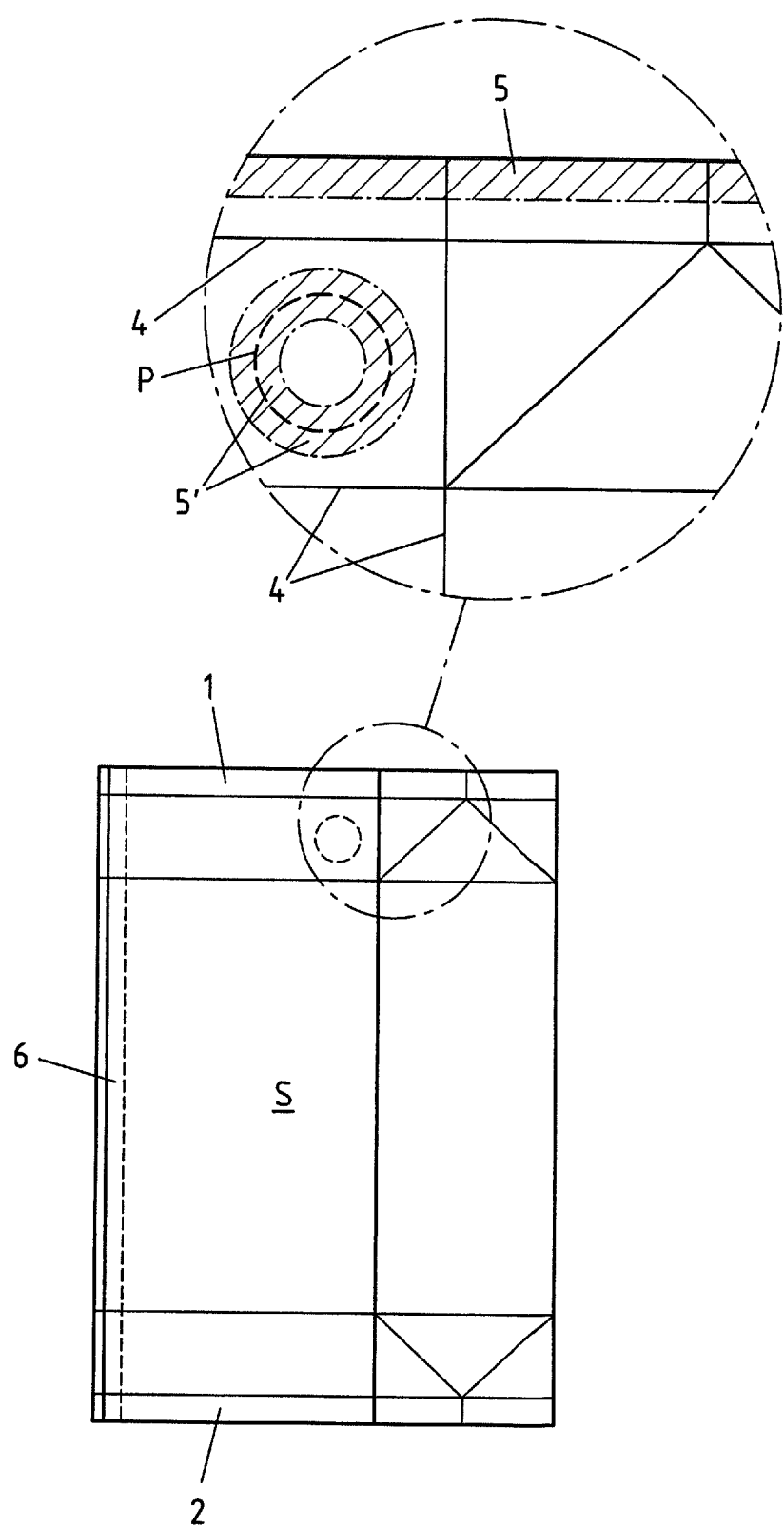
FIG. 1B shows a flat-folded packaging sleeve, produced from a blank according to
FIG. 1A.

FIG. 1B shows a packaging sleeve S, produced from a blank B according to FIG. 1A, said blank B having been joined in its seam region 3 to form a sheath by sealing a longitudinal seam 6 and having been folded flat to form a packaging sleeve S. The blank is folded flat simply because the packaging sleeves S are usually produced in another location compared to the subsequent further processing to produce beverage packagings, which processing is carried out in filling plants in different locations. For this purpose, a plurality of flat-folded packaging sleeves S is packed, standing upright, in so-called "covering boxes" 7 and is transported to the respective plants. The residence time of the packaging sleeves S in the covering boxes 7 up until they are opened directly in front of the filling machine is generally significantly longer than three days.

Figure 2:
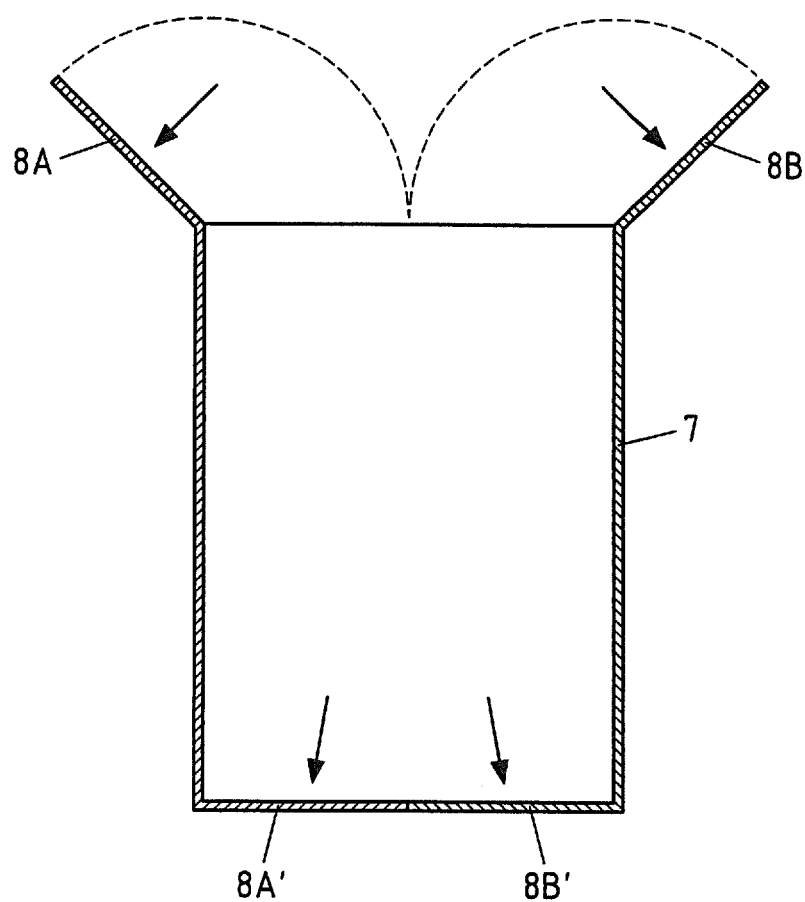
FIG. 2 is a vertical sectional view of a covering box for receiving a plurality of packaging sleeves with upwardly open cardboard flaps.

The invention has now recognised not to directly expose the open packaging edges, which are a problem in view of contamination, anymore at the top and bottom of the packaging sleeves S to a disinfectant, but to expose them in such way that at least some of the disinfectant-containing treatment agent is applied to a carrier element so that the actively sterilising atmosphere which is created then acts on the open cut edges and performs the desired sterilisation of the peripheral regions 5 of the edges or of the annular regions 5' of the packaging sleeves S. A covering box 7 of corrugated board can preferably be used as the carrier element, in which covering box the top and bottom flaps 8A and 8B, 8A' and 8B' are wetted on the inside of the cardboard with a treatment agent, more specifically in the region of the arrows in FIG. 2 which are not designated in more detail.

In this manner, created in the closed covering box 7 is an actively sterilising atmosphere in which the treatment agent can penetrate the open cut edges of the packaging sleeves S, or in which the cardboard material, located in the peripheral region or in a perforation at the open cut edges, is induced to absorb the treatment agent. There, the disinfectant penetrates to such an extent (a few millimetres) into the cardboard material that an adequate sterilisation is achieved.

Figure 3:
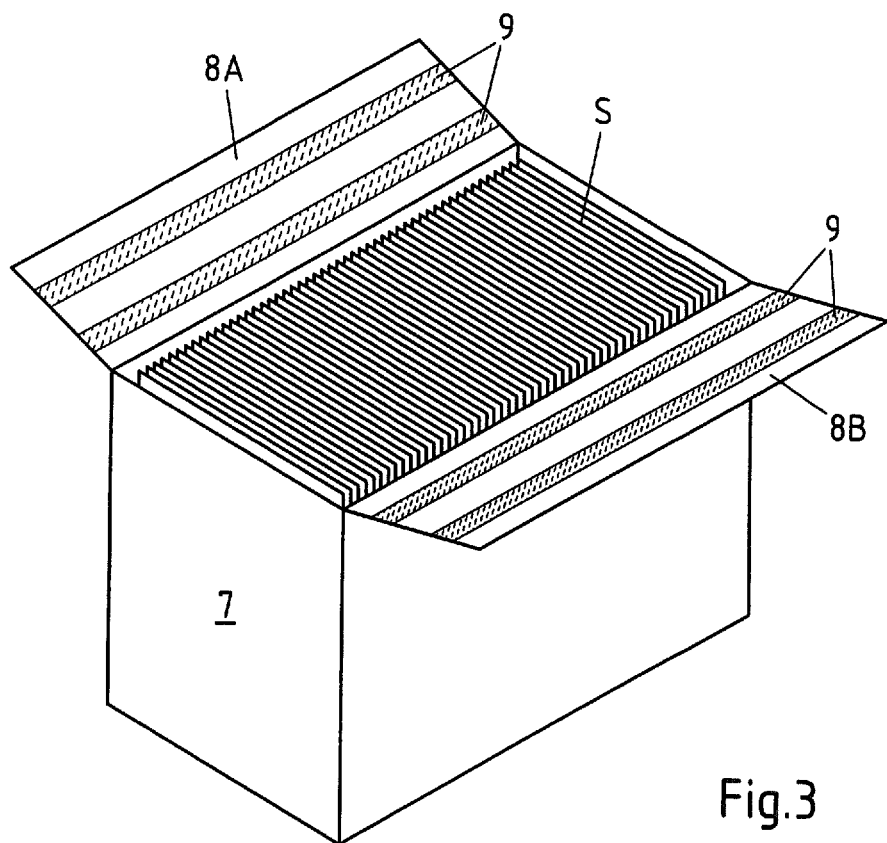
FIG. 3 is a perspective view of a first embodiment of an upwardly open covering box with flat-folded packaging sleeves located therein.

However, it is also possible that the treatment agent is not applied directly to the surface of the covering box 7 but is introduced there by means of a carrier element or a load carrier. For this purpose, for example strips 9, as shown in FIG. 3, consisting of adhesive tape, felt or other suitable materials can be affixed to the inside of the covering box 7 or can just be placed in the lower region of the covering box 7. It has been found that a full-surface wetting is not absolutely necessary to achieve a satisfactory saturation of the atmosphere with disinfectant.

Figure 4:
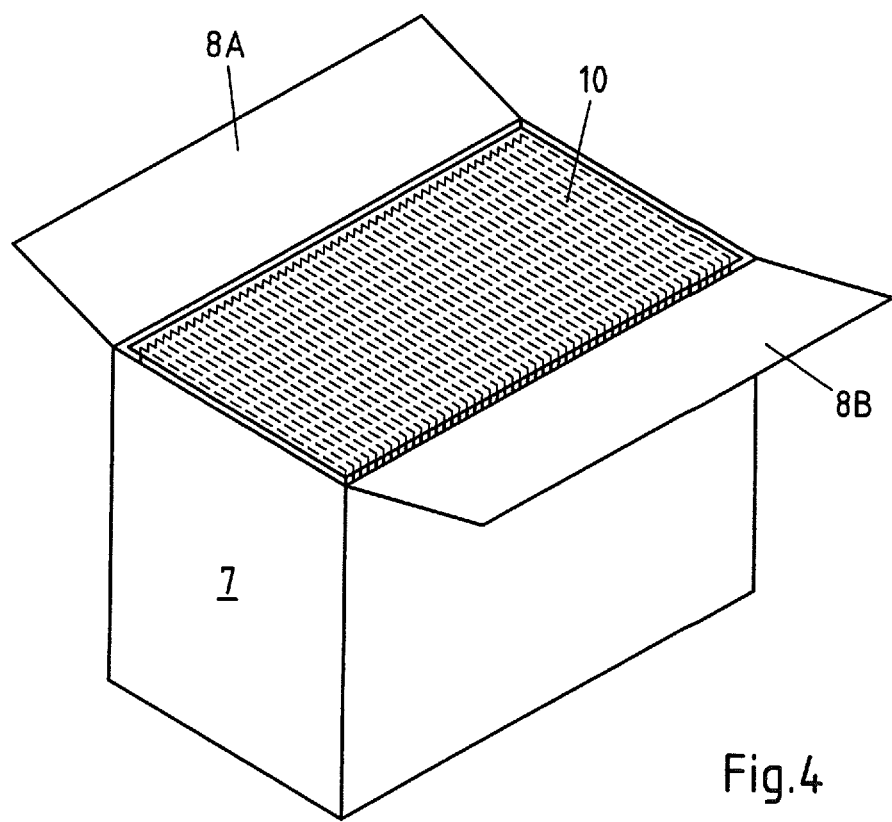
FIG. 4 is a perspective view of a second embodiment of an upwardly open covering box with flat-folded packaging sleeves located therein.

FIG. 4 shows that it is also possible to place an insert sheet 10 into the covering box 7 (at the top and/or bottom), said insert sheet 10 having been wetted with the required amount of treatment agent over its entire surface or just over a part thereof.

Figure 5:
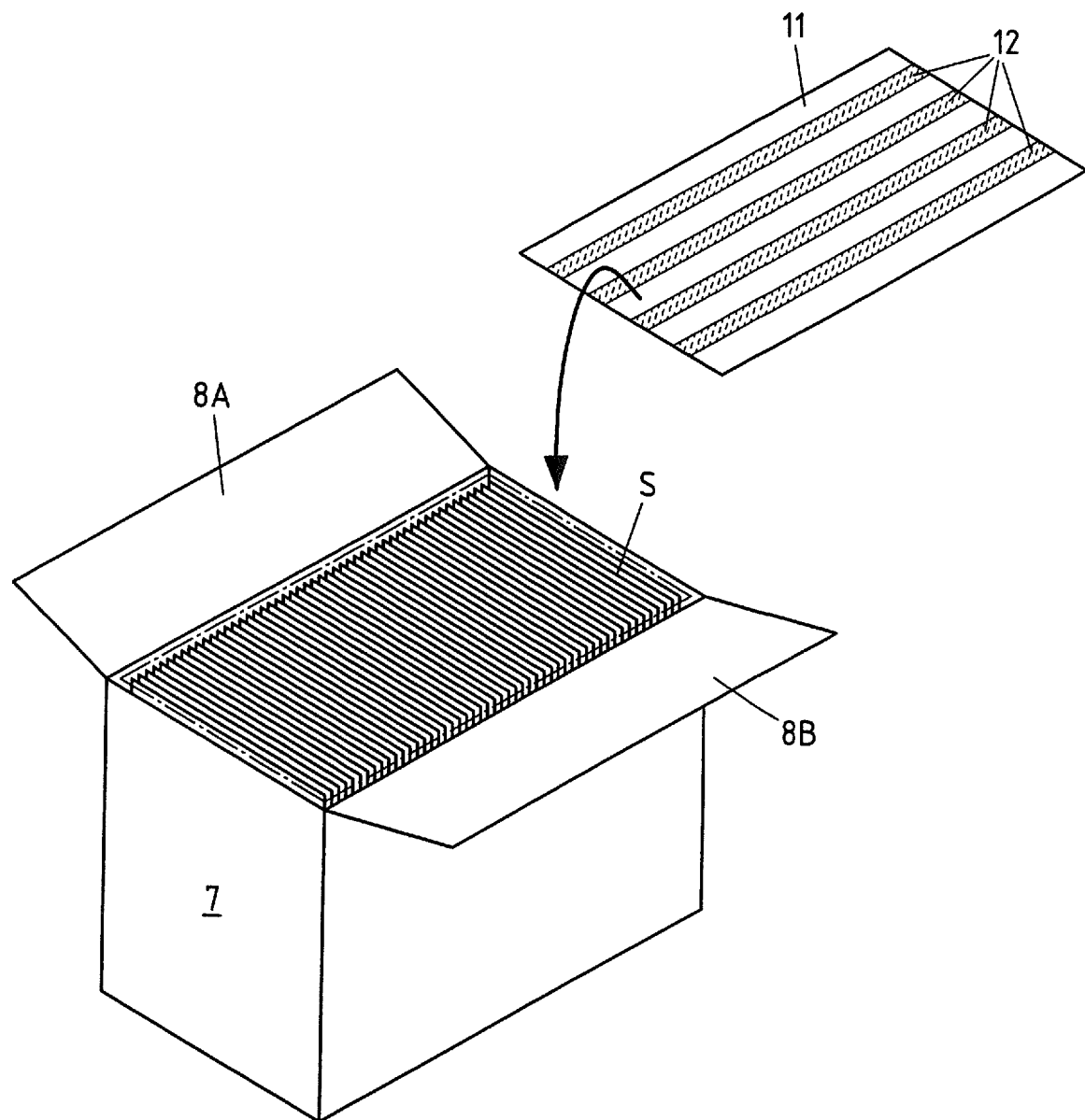
FIG. 5 is a perspective view of a further embodiment of an upwardly open covering box with flat-folded packaging sleeves located therein.

FIG. 5 shows that it is also possible to provide an insert sheet 11 with strip-shaped load carriers 12, which sheet 11 is then turned over and placed on the upper open cut edges of the packaging sleeves S before the covering box 7 is closed. Of course, it is also possible to place a correspondingly prepared insert sheet on the bottom of the covering box 7 before the packaging sleeves S are introduced into said box 7 in order to also disinfect the lower open cut edges of the packaging sleeves S.

It can be seen in FIG. 6 that the upright, flat-folded packaging sleeves S can also be transported in an "outer packaging" made of a plastics material. The figure clearly shows in a vertical sectional view a plastics container 13, on which a matching lid 14 has been placed. Inserted into the headspace of this outer packaging 7' is a prepared insert sheet 11' which serves as a load carrier, to achieve the necessary sterile atmosphere. To provide a better closure, the "open" transitions between container 13 and lid 14 can also be closed with adhesive tape.

It has not been shown that a plurality of upright, flat-folded packaging sleeves can be enclosed not by a fixed outer packaging, but by a shrink film, for example, in which case an appropriate insert of carrier material is previously introduced into the region of the open cut edges in order to carry out the desired sterilisation there.

FIG. 7 shows that it is also possible to treat a roll R of a composite packaging material, wound up onto a holder T, on its open edges by the method according to the invention. This is particularly advantageous when the roll width corresponds exactly to the packing height, because then the two circular areas of the roll consist almost over the entire surface of open cut edges. For this purpose, in the illustrated embodiment which is preferred in this respect, the roll R is enclosed by a two-part shrink cap consisting of a relatively small cap part 15 and a relatively large cap part 16, adapted thereto. It can also be seen here that insert sheets 11" are present in the region of the open cut edges to create the desired sterile atmosphere. Of course, it is also possible where the packaging of roll materials is concerned to package them in shrink film after they have been provided with load carriers 11", as previously described.

FIG. 8 shows on the example of the upper left-hand corner of the container from FIG. 6 that it is also possible to introduce as load carrier a slightly more voluminous strip 17 of felt material or the like and, in this case, the strip 17 can also be loaded with treatment agent after the container has been closed. For this purpose, a wall of the container is pierced by a needle and, in this manner, the internal strip 17 is saturated with the required amount of treatment agent in order to adequately sterilise the open cut edges of the ready packed, flat-folded packaging sleeves S. For this purpose, the container can have a channel-prepared opening 18. It is also possible to provide further strips 17' as load carriers in the headspace of the container, if required.

The invention claimed is:

1. A container for receiving a plurality of flat-folded packaging sleeves, blanks or web material, rolled up into a roll, wherein at least parts of an inside of the container are wetted with a treatment agent, and load carriers wetted with the treatment agent are provided inside the container, and wherein the treatment agent contains ethanol and a disinfectant, wherein the treatment agent is configured to be absorbed from the container and the load carriers into open cut edges of the flat-folded packaging sleeves, blanks or web material.

2. The container according to claim 1, wherein at least an outer surface of the container is sealed at least in a treated region.

3. The container according to claim 1, wherein cardboard is used as material for the container, and wherein the container comprises a covering box with one or more closable flaps.

4. The container according to claim 1, wherein plastics is used as material for the container.

5. The container according to claim 4, further comprising a plastics container and a plastics lid as well as at least one load carrier.

6. The container according to claim 4, further comprising a shrink film with load carriers.

7. The container according to claim 1, wherein the disinfectant comprises hydrogen peroxide solution.

* * * * *